United States Patent

Buysch et al.

Patent Number: 5,861,107
Date of Patent: Jan. 19, 1999

[54] PROCESS FOR THE PREPARATION OF ALIPHATIC CARBONATES HAVING A SIX-MEMBERED RING

[75] Inventors: Hans-Josef Buysch; Gerd Fengler, both of Krefeld; Karl-Heinz Neumann, Sankt Augustin; Paul Wagner, Düsseldorf; Martin Melchiors, Aachen; Wieland Hovestadt, Krefeld, all of Germany

[73] Assignee: Bayer Aktiengesellschaft, Leverkusen, Germany

[21] Appl. No.: 877,386

[22] Filed: Jun. 17, 1997

[30] Foreign Application Priority Data

Jun. 25, 1996 [DE] Germany ............... 196 25 265.2
Jul. 22, 1996 [DE] Germany ............... 196 29 462.2

[51] Int. Cl.$^6$ .................... C09K 3/00; C07D 321/00
[52] U.S. Cl. ............................. 252/182.29; 549/228
[58] Field of Search ................... 252/182.29; 549/228

[56] References Cited

U.S. PATENT DOCUMENTS

| | | |
|---|---|---|
| 3,790,648 | 2/1974 | Schmidt et al. . |
| 4,252,750 | 2/1981 | Buysch et al. . |
| 4,440,937 | 4/1984 | Krimm et al. . |
| 4,501,905 | 2/1985 | Krimm et al. . |
| 4,568,755 | 2/1986 | Mues et al. . |
| 4,694,065 | 9/1987 | Mues et al. . |
| 4,707,539 | 11/1987 | Mues et al. . |
| 4,754,017 | 6/1988 | Leitz et al. . |
| 4,912,198 | 3/1990 | Fontana ................. 528/370 |
| 5,142,024 | 8/1992 | Brunelle et al. ........ 528/371 |
| 5,212,321 | 5/1993 | Muller et al. ........... 549/228 |

FOREIGN PATENT DOCUMENTS

| | | |
|---|---|---|
| 0188204 | 7/1986 | European Pat. Off. . |
| 0236862 | 9/1987 | European Pat. Off. . |
| 0293690 | 12/1988 | European Pat. Off. . |
| 0422523 | 4/1991 | European Pat. Off. . |
| 0600417 | 6/1994 | European Pat. Off. . |
| 0665260 | 8/1995 | European Pat. Off. . |
| 0703230 | 3/1996 | European Pat. Off. . |
| 3418091 | 11/1985 | Germany . |
| 4109236 | 9/1992 | Germany . |

OTHER PUBLICATIONS 1,3–Dioxan–2 One–Group–Containing Oligourethanes, Le A 30,647–US, pp. 1 –15 (1996).

*Primary Examiner*—Johann Richter
*Assistant Examiner*—Joseph Murray
*Attorney, Agent, or Firm*—Sprung Kramer Schaefer & Briscoe

[57] ABSTRACT

The invention relates to a process for the preparation of carbonates having a six-membered ring, of the formula

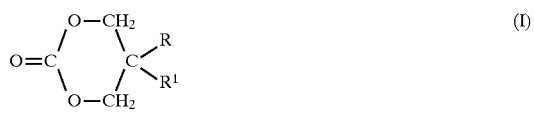

by transesterification of 1,3-propanediol compounds with carbonic acid esters and subsequent distillative depolymerization of the oligo- or polycarbonate initially formed, one or more catalysts from the group consisting of compounds of Sn, Ti or Zr being employed both for the transesterification and for the depolymerization and, if appropriate, the distillation residue is at least partly recycled into the transesterification. Such carbonates having a six-membered ring can furthermore be stabilized against undesirable polymerization by addition of small amounts of acids of sulfur or phosphorus or esters or salts thereof.

22 Claims, No Drawings

5,861,107

PROCESS FOR THE PREPARATION OF ALIPHATIC CARBONATES HAVING A SIX-MEMBERED RING

BACKGROUND OF THE INVENTION

1. Field of the Invention

The present invention relates to the preparation of cyclic carbonates having a 6-membered ring by transesterification of 1,3-propanediol compounds with carbonic acid esters and subsequent distillative depolymerization of the oligo- or polycarbonate initially formed, both stages being carried out in the presence of catalysts from the group consisting of Sn, Ti and Zr compounds and, if appropriate, the distillation residue of the depolymerization being at least partly recycled into the transesterification. The cyclic carbonates which can be prepared according to the invention can furthermore be stabilized against undesirable polymerization. The present invention therefore furthermore relates to cyclic carbonates thus stabilized, which have small amounts of acids of sulfur or phosphorus or esters or salts thereof and, when exposed to heat, show a significantly lower tendency toward polymerization than those which have not been stabilized.

2. Description of the Related Art

As is known, carbonates (I) having a six-membered ring can be obtained by transesterifying 1,3-propanediol compounds (II) with carbonic acid esters (III), the hydroxy compounds $R^3OH$ being split off, and depolymerizing the resulting oligo- or polycarbonates under the conditions of a vacuum distillation to give (I), and separating off and isolating (I). Such processes are described, for example, in U.S. Pat. No. 4,501,905 and U.S. Pat. No. 4,440,937. Strongly alkaline catalysts from the group consisting of oxides, hydroxides, alcoholates, carboxylates and carbonates of alkali metals (preferably Na and K), aluminum, thallium or lead are employed here for the transesterification. During the depolymerization, depending on the conditions applied, such as pressure, temperature and reaction apparatus, and the amount and nature of the catalysts used, a greater or lesser amount of a distillation residue of about 25 to, in the most favorable case, 5% of the oligo- or polycarbonate employed is obtained, which must be disposed of and accordingly reduces the yield of (I).

It has now been found that some of the disadvantages can be avoided by another reaction procedure, in which both the stage of transesterification and the stage of depolymerization are carried out in the presence of Sn, Ti or Zr compounds. To improve the process further, all or at least some of the distillation residue from the depolymerization can be employed again in the transesterification of (II) with (III), the amount of (II) and (III) employed for a particular amount of (I) can thus be reduced, and the yield of (I), based on (II) and (III) employed, can be increased accordingly.

As is known, cyclic carbonates can be converted into polycarbonates in the presence of various catalysts. In this context, reference may be made to the following publications: U.S. Pat. No. 4,501,905, U.S. Pat. No. 4,568,755, EP 236 862, U.S. Pat. No. 4,707,539, EP-188 204 and U.S. Pat. No. 4,252,750. Although such polymerizations proceed far more slowly, they nevertheless also already proceed noticeably without an additional catalyst if the cyclic carbonates are exposed to heat over a relatively long period of time, for example are kept in the molten state. In itself, such a polymerization does not have an adverse effect if a melt is in any case to be fed to a polycarbonate synthesis. However, such a tendency toward polymerization manifests itself in a very troublesome manner if a cyclic carbonate, for example, is to be stored in the molten state over a relatively long period of time for polymer reactions other than self-polymerization then to be carried out. The polymer content formed then also participates in such other reactions, but impairs their result, reduces reproducibility and can even cause unusable products. Even if copolymerization of various dioxanones are to be carried out, prepolymerization of individual dioxanones impairs the result of a copolymerization in an unforeseeable manner and at any rate complicates the polymerization process.

A particularly pronounced tendency toward oligomerization and polymerization is shown by the cyclic carbonates of trimethylolalkanes, i.e. 5-methylol-dioxanones of the formula (VI)

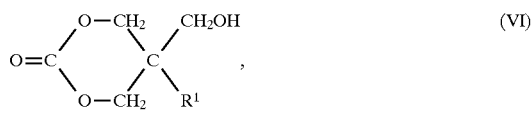

in which $R^1$ denotes $C_1$–$C_6$-alkyl, cyclohexyl or $C_6$–$C_{12}$-aryl.

The carbonate of trimethylolpropane, from which interesting paint bases can be prepared, may be mentioned above all (cf. EP 600 417, EP 665 260 and EP 703 230).

SUMMARY OF THE INVENTION

Surprisingly, it has now additionally been found that small additions of acids of sulfur and/or phosphorus or esters or salts thereof significantly slow down the rate of polymerization of the cyclic carbonates. The invention therefore furthermore relates to mixtures of cyclic carbonates with acids of sulfur and/or phosphorus and/or esters or salts thereof in the ratios of amounts stated below.

The invention relates to a process for the preparation of optionally stabilized cyclic carbonates of the formula (I)

in which

R and $R^1$ are identical or different and represent H, straight-chain or branched $C_1$–$C_6$-alkyl, $C_3$–$C_7$-cycloalkyl or —$CH_2$—$OR^2$, wherein $R^2$ represents H, $C_1$–$C_4$-alkyl, allyl, methallyl or benzyl and wherein two $R^2$ groups together can be —$CH_2$—, —CH($CH_3$)—, —CH($C_2H_5$)—, —CH($C_6H_5$)— or —CH($C_3H_7$)—, where $R^1$ can additionally denote $C_6$–$C_{12}$-aryl and where R and $R^1$ furthermore, together with the C atom on which they are substituents, can form a cyclopentane, cyclohexane, cycloheptane, oxetane, tetrahydrofuran, tetrahydropyran or dioxane ring, by transesterification of 1,3-propanediol compounds of the formula (II)

in which R and $R^1$ have the abovementioned meaning, with carbonic acid esters of the formula (III)

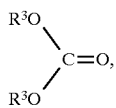

in which $R^3$ denotes $C_1$–$C_4$-alkyl or $C_6$–$C_{10}$-aryl, $R^3OH$ being split off, to give oligo- or polycarbonates and, by subsequent distillative depolymerization of the oligo- or polycarbonates thus obtained to give cyclic carbonates (I), which comprises carrying out both the stage of transesterification and the subsequent distillative depolymerization in the presence of one or more catalysts from the group consisting of tin, titanium and zirconium compounds in an amount of 0.001–5% by weight, preferably in an amount of 0.03–0.1% by weight, based on the total amount of (II) and (III), the transesterification being carried out at a temperature of 120°–180° C., preferably 150°–170° C., and the depolymerization being carried out at a temperature of 150°–280° C., preferably 190°–250° C., particularly preferably 200°–240° C., and the temperature for the depolymerization being 30°–150° C. above that of the transesterification, and, if appropriate, recycling 50–100% of the amount of distillation residue obtained in the depolymerization into the reaction of (II) with (III), it being possible to add to the cyclic carbonates (I) after the depolymerization, one or more compounds from the group consisting of acids of sulfur and phosphorus and esters and salts thereof in an amount of 0.001–5% by weight, based on the amount of (I) for stabilization against undesirable polymerization.

The invention also relates to mixtures of cyclic carbonates of the formula (I) with at least one compound from the group consisting of acids of sulfur and phosphorus and esters and salts thereof in amounts of 0.001 to 5% by weight of the sulfur and phosphorus compounds mentioned, based on the amount of cyclic carbonates, and optionally with an additional content of one or more solvents from the group consisting of ethers, esters, ketones, nitriles, amides, lactams and lactones, preferably from the group consisting of esters, amides, lactams and lactones, in an amount of 2 to 500%, preferably 3 to 300%, particularly preferably 5 to 200% of the total weight of cyclic carbonate and S or P compound.

Such mixtures preferably comprise cyclic carbonates of the formula (VI).

DETAILED DESCRIPTION OF THE INVENTION

Straight-chain or branched $C_1$–$C_6$-alkyl is, for example, methyl, ethyl, propyl, i-propyl, butyl, i-butyl, pentyl and its isomers or hexyl and its isomers. The preferred alkyl has 1–4 C atoms.

$C_3$–$C_7$-cycloalkyl is, for example, cyclopropyl, cyclobutyl, cyclopentyl, cyclohexyl or cycloheptyl, preferably cyclohexyl.

Alkyl and cycloalkyl can be substituted by OH and/or $OCH_3$ and/or $OC_2H_5$.

$C_6$–$C_{12}$-Aryl is, for example, phenyl, tolyl, xylyl, chlorophenyl, naphthyl or biphenyl, and the preferred aryl is phenyl, tolyl or chlorophenyl; phenyl is particularly preferred.

The substituents $R^{10}$ and $R^{11}$ preferably occur instead of R and $R^1$. $R^{10}$ and $R^{11}$ are identical or different and denote H, $CH_3$, $C_2H_5$ or —$CH_2$—$OR^2$, wherein $R^2$ has the above meaning.

Examples of (II) which may be mentioned are propane-1,3-diol, 2-ethylpropane-1,3-diol, 2,2-dimethyl-propane-1,3-diol, 1,1-dimethylol-cyclohexane, trimethylolethane, trimethylolpropane, pentaerythritol, trimethylolpropane monomethyl ether, trimethylolpropane monoethyl ether, trimethylolpropane monobenzyl ether, trimethylolpropane monoallyl ether and pentaerythritol formal of the formula (IV) and 3,3-dimethyloloxetane of the formula (V)

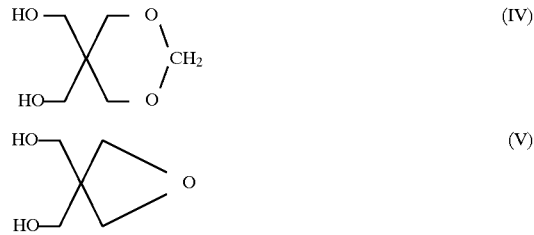

Suitable carbonic acid esters are those of the formula (III) in which $R^3$ denotes $C_1$–$C_4$-alkyl or aryl, i.e. dimethyl, diethyl, dipropyl, diisopropyl, dibutyl-, diisobutyl, diphenyl and dicresyl carbonate and dinaphthyl carbonate.

The transesterification of the starting products according to (II) and (III) takes place by the processes described in U.S. Pat. No. 4,501,905 and U.S. Pat. No. 4,440,937 and is carried out in the temperature range of 60°–250° C., under normal pressure or under reduced pressure, preferably in the range of 0.001–140 mbar, and in the presence of catalysts from the group consisting of alkalis, tin compounds and titanium compounds, which are mentioned in U.S. Pat. No. 4,501,905 and U.S. Pat. No. 4,440,937.

The subsequent distillative depolymerization of the oligo- or polycarbonate initially obtained with structural units of the formula (I) is carried out in the temperature range of 150°–280° C., preferably in the temperature range of 190°–250° C., particularly preferably 200° C.–240° C., in the pressure range of 0.01–20 mbar and in the presence of catalysts from the group consisting of alkalis and tin compounds and titanium compounds which are mentioned in U.S. Pat. No. 4,501,905 and U.S. Pat. No. 4,440,937. The depolymerization is particularly preferably carried out in the form of a flash distillation, i.e. the molten oligopolycarbonate is metered into a heated reactor and the monocarbonate vapors formed are condensed immediately. During this procedure, monomeric (I) distils off, and a distillation residue remains which, according to the invention, is recycled at least partly, i.e. to the extent of 50–100%, preferably 60–100%, particularly preferably 70–100% of its amount, into the transesterification of (II) with (III).

It may be advantageous to dissolve the distillation residue from the depolymerization, which is to be recycled into the transesterification reaction, beforehand in the amount of (II) to be employed, or a portion thereof, and only then to add the carbonate (III) to the transesterification. This proves expedient if the residue has a very high molecular weight or is completely or partly crosslinked. As a rule, however, this measure is not necessary. The transesterification can then otherwise be carried out in accordance with the abovementioned instructions.

The amount of residue which can be recycled into the transesterification depends of course on the composition and quality thereof, which can be determined by hydrolysis and analysis of the hydrolysis products by gas chromatography, or by NMR spectroscopy, or also purely empirically, by employing a larger or smaller amount of the residue in the transesterification reaction by way of trial and investigating the influence thereof on the depolymerization and the purity of the resulting carbonate having a six-membered ring. The expert will quickly be able to determine the appropriate amount of recyclable residue in this manner.

This type of utilization of the residue is particularly interesting for synthesis of those carbonates having a six-membered ring of which depolymerization is particularly demanding and can give rise to the formation of relatively large amounts of residue. These are, in particular, the triols from the series consisting of the trimethylolalkanes and pentaerythritol of the formulae

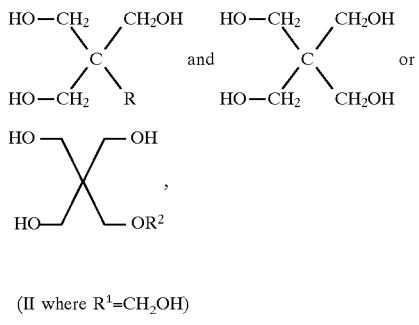

(II where $R^1=CH_2OH$)

(II where $R=R^1=CH_2OH$), since during depolymerization thereof, high molecular weight or even crosslinked structures can easily form. The process according to the invention is especially important for the preparation of trimethylolpropane monocarbonate, from which novel high-performance paint bases can be prepared, as has already been mentioned above.

Acids of sulfur and esters or salts thereof which can be employed according to the invention in the case where stabilization is envisaged are those of the formula

wherein
the indices m, n, o and p independently of one another denote the figure zero or one, but only two of these indices may simultaneously be zero, X represents $H^\oplus$, $Li^\oplus$, $Na^\oplus$, $K^\oplus$, $Rb^\oplus$, $Cs^\oplus$ or $N(R^3, R^4, R^5, R^6)^\oplus$, wherein $R^3$ to $R^6$ independently of one another denote H, $C_1$–$C_{18}$-alkyl, phenyl or benzyl, or represents $C_1$–$C_{18}$-alkyl, $C_6$–$C_{12}$-aryl or benzyl, where alkyl, aryl and benzyl can be substituted once or twice by methyl, ethyl, chlorine or $SO_3H$, and $R^2$ assumes the meaning of —OX, —OOH, —OSO₃, —OOSO₃, —NH₂, —NH(SO₃H), $C_1$–$C_{18}$-alkyl or $C_6$–$C_{12}$-aryl, which can be substituted in the manner mentioned, where, in the case where $R^2$ denotes OX, not all the X denote one of the metal cations mentioned, and where $R^2$, in the case where n denotes zero, can also represent double-bonded oxygen.

Such acids of sulfur are, for example, sulfurous acid, sulfuric acid, their anhydrides $SO_2$ and $SO_3$, aliphatic and aromatic mono- and polysulfonic acids and sulfenic or sulfinic acids having 1 to 18 C atoms, which can be partly neutralized and accordingly can be present as the partial salt or half-salt, peroxysulfuric acid, amidosulfonic acids, disulfuric acid and peroxydisulfuric acid and half-salts thereof with alkalis, ammonia and amines, aminomethanesulfonic acids and hydroxy-methanesulfonic acids, such as are described, for example, in Houben-Weyl, Methoden der organ. Chemie, [Methods of organic chemistry], Volume 9, pages 267, 281–3, 289–97.

In formula (III), preferably p=1, particularly preferably p and m=1, and especially preferably p, m and n=1.

Acids of phosphorus and esters or salts thereof which can be employed according to the invention in the case where stabilization is envisaged are those of the formula

wherein
m denotes the number zero or one, $R^7$ represents $C_1$–$C_{20}$-(cyclo)alkyl, $C_6$–$C_{12}$-aryl or $C_7$–$C_{10}$-aralkyl, which can be substituted once or twice by O—$C_1$–$C_4$-alkyl, S—$C_1$–$C_4$-alkyl, COOH, CN, Cl, Br, $NH_2$, NH—$C_1$–$C_4$-alkyl, $N(C_1$–$C_4$-alkyl)$_2$, NH—$C_6H_5$, $N(C_1$–$C_4$-alkyl-P(O)(OH)$_2)_2$ or P(O)(OH)$_2$ or two different radicals of these, and in the (cyclo)alkyl contents of which one or two C atoms can be replaced by —O—, —S—, —NH—, —N($C_1$–$C_4$-alkyl)— or —CO— and/or two C atoms can be linked by a double or triple bond, and $R^8$ and $R^9$ independently have the meaning OX, wherein X assumes the scope of meaning mentioned above in connection with formula (III), including the limitation with respect to the metal cations if two X are present, but wherein, in the context of the formula (IV), the substituent P(O)(OH)$_2$ occurs instead of the substituent $SO_3H$, and wherein $R^8$ furthermore can assume the scope of meaning of $R^7$ and $R^9$ can also denote H, and wherein $R^7$ and $R^8$ furthermore together can represent —O-arylene-O— or -arylene-O—, wherein arylene represents biphenylyl or —$C_6H_4$—$C_1$–$C_6$-(cyclo)alkylene-$C_6H_4$—.

Such acids of phosphorus are, for example, compounds with the characteristic groups

(cf. Houben-Weyl, Methoden der organischen Chemie [Methods of organic chemistry], Volume 12/1, page 197),

(ibid., pages 223, 227–8, 235, 238, 249, 255–7)

(ibid., pages 295, 322–3, 326–7, 329) or

(ibid., pages 350, 355–6, 362, 365–6, 368–70, 374–82, 426–7, 444–5, 451–2, 466–73, 478–81, 485–7),
wherein $R^7$, $R^8$ and $R^9$ have the meaning given.

The following list shows which compounds in the context of the present invention can be employed as acids, esters and salts of phosphorus having a stabilizing action, wherein the designations R, R', $R^1$ etc., A, X and others do not agree with the above substituent designations but are to be found in the publications cited:

1) 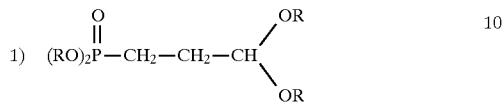

(German Offenlegungsschrift 25 17 448)

2) 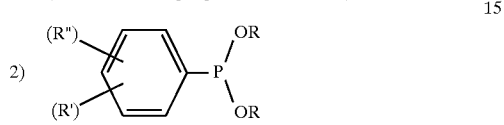

(German Offenlegungsschrift 28 34 871)

3) 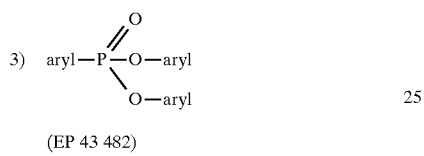

(EP 43 482)

4) 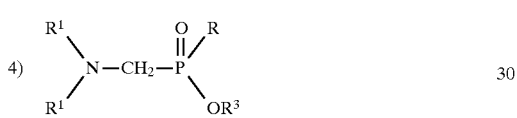

(Phosphorus and Sulfur 14 (1983), 295–322)

5) 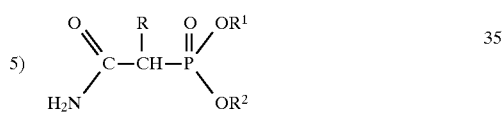

(German Offenlegungsschrift 34 45 300)

6) 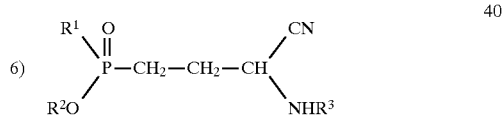

(German Offenlegungsschrift 35 08 573)

7) 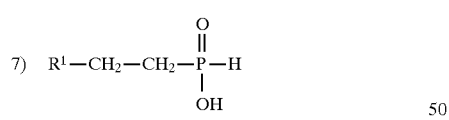

(EP 246 015)

8) 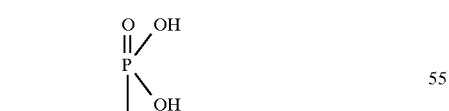

(EP 243 173; EP 275 821)

9) 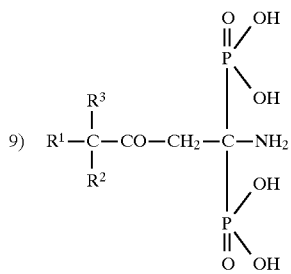

(German Offenlegungsschrift 36 11 522)

10) 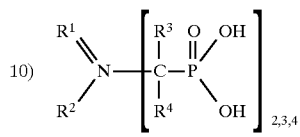

(German Auslegeschrift 12 14 229)

11) 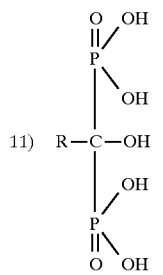

(German Auslegeschrift 11 48 235)

12) 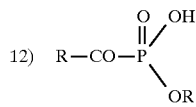

(German Auslegeschrift 10 10 965)

13) 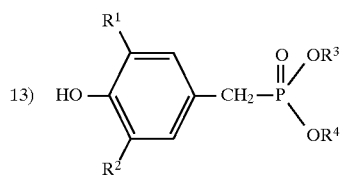

(German Offenlegungsschrift 22 03 837; German Offenlegungsschrift 24 45 323)

14) 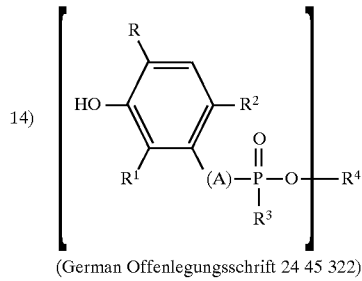

(German Offenlegungsschrift 24 45 322)

-continued
15) 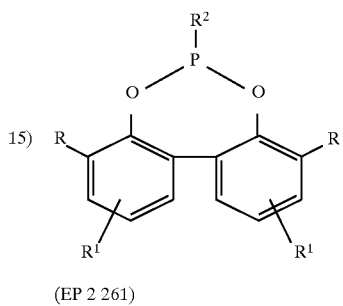
(EP 2 261)
16) 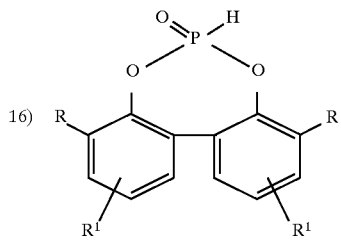
(German Offenlegungsschrift 28 56 801)
17) 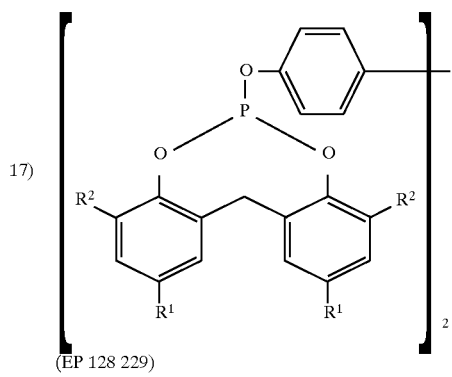
(EP 128 229)
18) 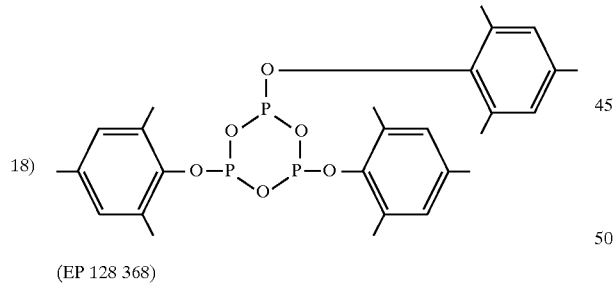
(EP 128 368)
19) 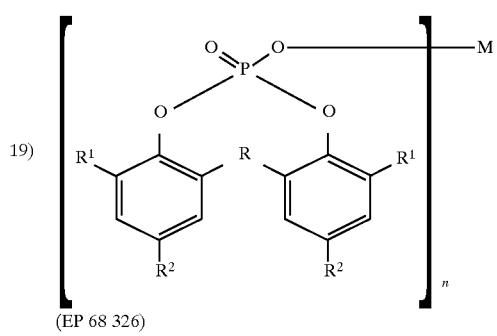
(EP 68 326)
20) 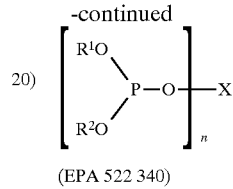
(EPA 522 340)
21) 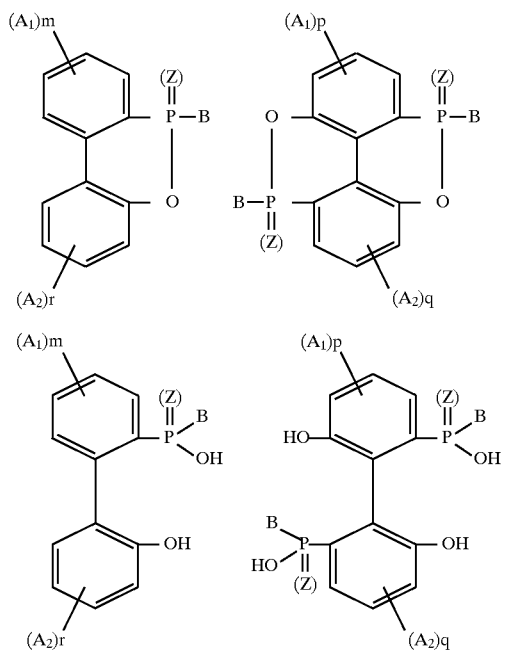
(EPA 522 340)
22) 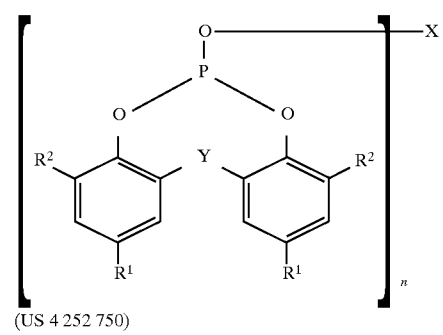
(US 4 252 750)
23) 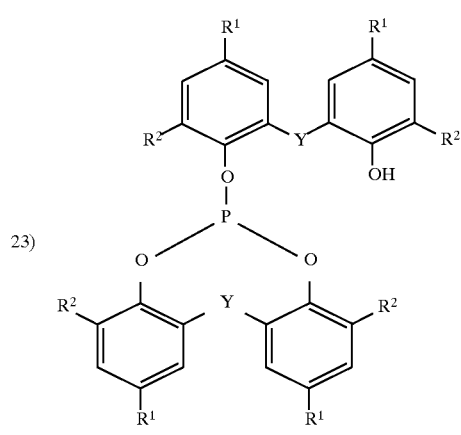
(EP 617 041)

24) Hypophosphorous acid, phosphorous acid, phosphoric acid, which can be partly and completely esterified and/or partly neutralized by alkali metal, alkaline earth metal and nitrogen bases (cf. Houben-Weyl, volume 12/2, pages 8, 24–5, 56–7, 61, 65–7, 173, 191–8, 209–10, 236, 250, 258, 260, 277, 309, 330–1).

Preferred compounds are those having the structure 2), 4), 5), 7), 8) to 13), 16), 17), 19) and 20) to 24), particularly preferably the structure 4), 8) to 11), 17), 21) to 24), especially preferably the structure 10), 17), 21), 22) and 24).

Furthermore, in formula (IV), preferably m=1.

Of the compounds of sulfur and phosphorus mentioned, those of phosphorus are preferred. A non-exhaustive list of individual compounds given by way of example is the following: dioctyl-phosphinous acid, dihexylphosphinous acid, dibenzylphosphinous acid, dicyclohexylphosphinous acid, diphenyl-phosphinous acid, bis-(4-chlorophenyl) phosphinous acid, bis-(4-methoxyphenyl)phosphinous acid, diethyl-phosphinic acid, dipropyl-phosphinic acid, diisopropyl-phosphinic acid, dibutyl-phosphinic acid, dihexyl-phosphinic acid, dioctyl-phosphinic acid, diphenyl-phosphinic acid, bis-(4-methoxy-phenyl)-phosphinic acid, dimethyl-phosphinic acid, methyl-butyl-phosphinic acid, methyl-phenyl-phosphinic acid, [3-oxo-1,5-diphenyl-penten-(4)-yl-(1)]-phenylphosphinic acid, [4-oxo-2-methyl-pentyl-(2)]-phenyl-phosphinic acid, [3-oxo-1,5-diphenyl-propyl-(1)]butyl-phosphinic acid, phenyl-(3-chlorophenyl) phosphinic acid, phenyl-(3-aminophenyl)phosphinic acid, phenyl-(2-carboxy-phenyl)-phosphinic acid, diethyl-phosphinic acid ethyl ester, dipropyl-phosphinic acid propyl ester, dibutyl-phosphinic acid butyl ester, ethyl-butyl-phosphinic acid ethyl ester, carbethoxymethyl-ethyl-phosphinic acid ethyl ester, butylbenzyl-phosphinic acid ethyl ester, methyl-phenyl-phosphinic acid methyl ester, ethane-phosphonous acid, propane-phosphonous acid, 2-methylpropane-phosphonous acid, phenylmethane-phosphonous acid, triphenylmethane-phosphonous acid, 2-phenyl-ethylene-phosphonous acid, benzene-phosphonous acid, 4-methyl-benzene-phosphonous acid, 4-ethyl-benzene-phosphonous acid, 2,4,6-trimethyl-benzene-phosphonous acid, 4-chloro-benzene-phosphonous acid, 4-methoxy-benzene-phosphonous acid, naphthalene-1-phosphonous-acid, ethane-phosphonous acid monomethyl ester, benzene-phosphonous acid monobutyl ester, benzene-phosphonous acid monobenzyl ester, methane-phosphonous acid diphenyl ester, ethane phosphonous acid diphenyl ester, benzene-phosphonous acid diphenylester, naphthalene-1-phosphonous acid diphenyl ester, 2-phenylethylene-phosphonic acid, 2,2-diphenyl-ethylene-phosphonic acid, methane-phosphonic acid, ethane-phosphonic acid, propane-1-phosphonic acid, butane-1-phosphonic acid, butane-2-phosphonic acid, phenylmethane-phosphonic acid, (4-methyl-phenyl)methane-phosphonic acid, β-naphthyl-methane-phosphonic acid, 2-phenoxy-ethane-phosphonic acid, 4-oxo-2-methyl-pentan-2-phosphonic acid, diethylamino-methane-phosphonic acid, diphosphono-methane-(methane-diphosphonic acid), 1,2-diphosphono-ethane-(ethane-1,2-diphosphonic acid), 4-oxo-2-methyl-pentane-2-phosphonic acid, 3-oxo-2,5-dimethyl-cyclopentane-1-phosphonic acid, 3-oxo-1-methyl-cyclohexane-1-phosphonic acid, hydroxymethane-phosphonic acid, 1-hydroxy-ethane-1-phosphonic acid, 1-hydroxy-2-methyl-propane-1-phosphonic acid, α-hydroxy-phenylmethane-phosphonic acid, 2-hydroxy-propane-2-phosphonic acid, 1-hydroxy-1-phenyl-ethane-1-phosphonic acid, α-hydroxy-diphenylmethane-phosphonic acid, 1-hydroxy-1-carboxy-ethane-1-phosphonic acid, 1-hydroxy-cyclohexane-1-phosphonic acid, benzene-phosphonic acid, 3-methyl-benzene-phosphonic acid, 4-methyl-benzene-phosphonic acid, 4-tert-butyl-benzene-phosphonic acid, biphenyl-4-phosphonic acid, 2-fluoro-benzene-phosphonic acid, 4-chloro-benzene-phosphonic acid, 4-bromo-benzene-phosphonic acid, 4-fluoro-benzene-phosphonic acid (toluidine salt), 2,3-dichloro-benzene-phosphonic acid, 2,5-dichloro-benzene-phosphonic acid, 2-methoxy-benzene-phosphonic acid, 4-methoxy-benzene-phosphonic acid, 4-ethoxy-benzene-phosphonic acid, propene-2-phosphonic acid, phenoxy-methane-phosphonic acid, (bis-[2-hydroxyethyl]-amino)-methane-phosphonic acid, 1,3-bis-[N-phosphonomethyl-N-butylamino]-propane, 2-methylamino-propane-2-phosphonic acid, cyclohexane-phosphonic acid diphenyl ester, benzene-phosphonic acid diphenyl ester, 2-oxo-2-phenyl-4,5-benzene-1,3,2-dioxaphospholine, ethylene-phosphonic acid diethyl ester, ethylene-phosphonic acid diphenyl ester, propene-2-phosphonic acid dimethyl ester, 3-oxo-cyclohexane phosphonic diethyl ester, 3-oxo-1,5,5-trimethyl cyclohexane phosphonic dibutyl ester, 2-cyano-ethane-phosphonic acid dimethyl ester, 2-carbomethoxy-ethane-phosphonic acid dimethyl ester, 4-oxo-pentane-2-phosphonic acid dimethyl ester, 4-oxo-2-methyl-pentane-2-phosphonic acid dimethyl ester, 2-oxo-heptane-4-phosphonic acid dibutyl ester, 3-oxo-1-phenyl-butane-1-phosphonic acid dimethyl ester, 3-oxo-1-phenyl-butane-1-phosphonic acid diethyl ester, 1,2-dicarbomethoxy-ethane-phosphonic acid dimethyl ester, 1,2-dicarboethoxy-propane-2-phosphonic acid diethyl ester, 1-amino-propane-1-phosphonic acid diethyl ester, 1-diethylamino-propane-1-phosphonic acid diethyl ester and 1-diethylamino-2-propene-1-phosphonic acid diethyl ester.

The amounts of the abovementioned compounds used for the stabilization are 0.001 to 5% by weight, based on the weight of the cyclic carbonate, preferably 0.005 to 3, particularly preferably 0.01 to 2% by weight.

The stabilizer can be distributed in the carbonate directly by introduction into the melt or the solution of the carbonate, or by first preparing a masterbatch, a concentrate of the stabilizer in the carbonate or in a solvent, and then adding this in an appropriate dosage to the amount of carbonate to be stabilized.

Suitable solvents for the solution of the carbonate and of the stabilizer are inert polar solvents, such as ethers, esters, ketones, nitriles, amides, lactams and lactones. Examples which may be mentioned are ethyl (or butyl) acetate, diethyl carbonate, butyrolactone, N-methylpyrrolidone, dimethylacetamide, acetonitrile and 2-methoxy-propyl acetate. A mixture of several of the solvents mentioned can also be employed. These solvents have a total number of C atoms of 2–20, preferably 2–18, particularly preferably 2–12. Solvents of this type are known to the expert.

The co-use of a solvent is advantageous because the tendency towards polymerization is further reduced as a result. The present invention therefore also relates to the co-use of a solvent from the group of the abovementioned solvents in the stabilization of carbonates. Esters, lactones, amides and lactams are preferably used. The amount of solvent is 2 to 500%, preferably 3 to 300%, particularly preferably 5 to 200% of the total weight of carbonate having a six-membered ring and stabilizer.

EXAMPLE 1

1610 g (12 mol) of trimethylolpropane (TMP) and 2677 g (12.5 mol) of diphenyl carbonate (DPC) were transesterified with one another in the presence of 2 g of dibutyltin oxide at 150° to 160° C. under 20 to 30 mbar in a 4 l three-necked flask with a stirrer, thermometer and a silvered column about 80 cm long filled with Raschig rings, and the phenol formed was distilled off. When the splitting off of phenol had ended, the last residues of phenol were removed over a simple distillation bridge while blowing in nitrogen under 2–30 mbar at 160° to 165° C. 1880 g of TMP oligocarbonate remained in the transesterification flask.

150 ml/h of this were introduced continuously from a dropping funnel, heated at 150° to 160°, into a 1 l three-necked flask with a high-speed blade stirrer reaching the base and a thermometer. The flask was heated all round to 220° to 240° and evacuated to 2 mbar. The TMP carbonate vapors formed by cleavage of the oligomer were removed over a simple distillation bridge, condensed immediately and collected in a receiver. During the continuous cleavage, some of the bottom product which forms was removed from time to time.

Overall, 1650 g of the above TMP oligocarbonate were introduced into the cleavage flask and converted into TMP carbonate. 1351 g of distillate which comprised TMP carbonate to the extent of about 97% and TMP to the extent of 2 to 3% and 286 g of viscous distillation bottom product were obtained. This corresponded to a distillate yield of 82%; the loss was 13 g. The residue comprised 31.7% of $CO_2$ (carbonate group); pure TMP carbonate is calculated as 27.2%. The residue dissolved on heating in TMP.

EXAMPLE 2

Example 1 was repeated, 1610 g of TMP, 2636 g of DPC and the distillation residue from Example 1 being employed. The DPC content was reduced compared with Example 1 in accordance with the increased carbonate content of the residue, which also comprised the catalyst.

The transesterification was carried out analogously to Example 1, 2121 g of TMP oligocarbonate being formed. This was cleaved analogously to Example 1, for which a total of 1954 g were employed. 1590 g of distillate and 356 g of distillation residue were obtained. This corresponded to a distillation yield of about 81% at a loss of 8 g. The distillate comprised 97% of TMP carbonate and 2 to 3% of TMP. The yield for Example 1 was thus just above 99%, and for both experiments above 90%.

It was thus shown that the distillation residue can be converted almost completely into TMP carbonate. If used again and again, however, a greater or lesser proportion of the residue is advantageously removed and disposed of, depending on its composition. Nevertheless, the total yield of distillate is at any rate significantly above 95%.

EXAMPLE 3

In an apparatus analogous to Example 1, 1232.2 g (9.00 mol) of trimethylolpropane (TMP), 98% pure, and 2105.1 g (9.73 mol) of diphenyl carbonate, 99% pure, were transesterified with one another in the presence of 1.8 g of titanium tetrabutoxide at 150°–160° C. under a pressure of 20 mbar and the phenol formed was distilled off. When the splitting off of the phenol had ended, the last residues of phenol were removed over a simple distillation bridge, while blowing in nitrogen under 2–20 mbar at a bottom temperature of 170° C.

1470 g of TMP oligocarbonate remained in the transesterification flask.

1450 g of the TMP oligocarbonate were introduced continuously at a rate of 120 ml/h from a dropping funnel, heated at 160° C., into a 1 l four-necked flask with a high-speed blade stirrer which reached the bottom and a thermometer.

The cleavage flask was immersed up to the ground connectors in an oil bath heated at 240° C., and the apparatus was evacuated to 0.5–1.5 mbar. The TMP carbonate vapors formed by cleavage of the oligomer were passed through a Vigreux column, heated at 240° C., to a distillation condenser, condensed there and collected in a receiver. After about 700 g of TMP oligocarbonate had been dripped in, the flash distillation was interrupted and the distillation bottom product was poured out of the flask while still hot. The remaining amount of precursor, about 750 g, was then subjected to flash distillation in the same flask.

About 1200 g of oily distillate which crystallized in the course of time were obtained. The product has the following composition:

TMP Carbonate: 92%

TMP: 1.0%

3-Ethyl-hydroxymethyl-oxetane: 0.5%

Phenol: <0.3%

Remainder: Oligo-TMP carbonate

This corresponded to 76.6% of the theoretical yield of cyclic TMP carbonate, based on the TMP employed.

EXAMPLE 4 (COMPARISON)

In each case 30 g of crystalline, polymer-free trimethylolpropane monocarbonate (TMP-C) (melting point 41° C.) were heated in ampoules under $N_2$ at various temperatures for 48 hours and the non-polymerized proportions of TMP-C were then measured by gel chromatography and stated in % of the precursor:

50° C.: 95% of non-polymerized TMP-C

65° C.: 87% of non-polymerized TMP-C

80° C.: 68% of non-polymerized TMP-C

100° C.: 29% of non-polymerized TMP-C

EXAMPLES 5 TO 12

Example 4 was repeated, but 0.03 g (~0.1% by weight) of a stabilizer was admixed to the TMP-C in each ampoule. All ampoules were heated at 100° C. for 48 hours and then analyzed as described in Example 4:

| Example/stabilizer | Structure | % by weight |
|---|---|---|
| 5) [bis(cyclohexyl-methylphenol) phosphonate structure with O=P-H, two O linkages to substituted phenyl rings bridged by CH₂, each ring bearing cyclohexyl and methyl groups] | 22) | 93 of non-polymerized TMP-C |
| 6) $(CH_3O)_2P(=O)H$ | 24) | 89 of non-polymerized TMP-C |
| 7) $H_3PO_3$ | 24) | 80 of non-polymerized TMP-C |
| 8) [biphenyl cyclic phosphonate with P(=O)H] | 21) | 73 of non-polymerized TMP-C |
| 9) $P(-O-C_6H_5)_3$ | 24) | 67 of non-polymerized TMP-C |
| 10) $CH_3-C_6H_4-SO_3H$ | | 58 of non-polymerized TMP-C |
| 11) $[(HO)_2OP-CH_2]_2N-[(CH_2)_6-H_8]_2$ | 10) | 92 of non-polymerized TMP-C |

It can be seen that the polymerization was inhibited significantly, compared with Example 4, by the stabilizers.

EXAMPLES 12 TO 14

Example 5 was repeated, but the proportion of stabilizer in the TMP-C and the temperature were changed. The time (48 hours) was retained.

12) Stabilizer as in Example 11, 65° C.

| Amount of stabilizer | 0.1 | 0.05 | 0.02% |
|---|---|---|---|
| non-polymerized TMP-C | 98% | 97% | 97% |

13) Stabilizer as in Example 5, 65° C.

| Amount of stabilizer | 0.1 | 0.05 | 0.02% |
|---|---|---|---|
| non-polymerized TMP-C | 97% | 98% | 97% |

14) Stabilizer as in Example 6, 100° C.

| Amount of stabilizer | 0.5 | 0.2 | 0.1 | 0.05% |
|---|---|---|---|---|
| non-polymerized TMP-C | 98% | 97% | 85% | 83% |

The various concentrations of stabilizers provide good protection against undesirable polymerizations.

EXAMPLES 15 TO 17

In each case 30 g of crystalline, polymer-free TMP-C (melting point 41° C.) were dissolved in 30 g of butyl acetate (Example 15), 30 g of methoxypropyl acetate (Example 16) or 30 g of N-methylpyrrolidone (Example 17), in each case 0.1% of stabilizer from Example 5 was added and the mixtures were heated at 100° C. for 48 hours analogously to Example 5. The stabilized samples were practically unchanged. In comparative experiments without a stabilizer, the monomer content dropped to 80 to 85%.

What is claimed is:

1. A process for the preparation of an optionally stabilized cyclic carbonate of the formula (I)

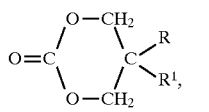 (I)

in which
R and $R^1$ are identical or different and represent H, straight-chain or branched $C_1$–$C_6$-alkyl, $C_3$–$C_7$-cycloalkyl or —$CH_2$—$OR^2$, wherein $R^2$ represents H, $C_1$–$C_4$-alkyl, allyl, methallyl or benzyl and wherein two $R^2$ groups together can be —$CH_2$—, —CH($CH_3$)—, —CH($C_2H_5$)—, —CH($C_6H_5$)— or —CH($C_3H_7$)—, where R' can additionally denote $C_6$–$C_{12}$-aryl and where R and $R^1$ furthermore, together with the C atom on which they are substituents, can form a cyclopentane, cyclohexane, cycloheptane, oxetane, tetrahydrofuran, tetrahydropyran or dioxane ring, by transesterification of a 1,3-propanediol compound of the formula (II)

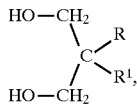 (II)

in which R and $R^1$ have the abovementioned meaning, with a carbonic acid ester of the formula (III)

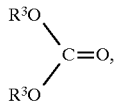 (III)

in which $R^3$ denotes $C_1$–$C_4$-alkyl or $C_6$–$C_{10}$-aryl, $R^3$OH being split off, to give an oligo- or polycarbonate and, by subsequent distillative depolymerization of the oligo- or polycarbonate thus obtained, to give a cyclic carbonate (I), which comprises carrying out both the stage of transesterification and the subsequent distillative depolymerization in the presence of one or more catalysts selected from the group consisting of titanium and zirconium compounds in an amount of 0.001–5% by weight, based on the total amount of (II) and (III), the transesterification being carried out at a temperature of 120°–180° C. and the depolymerization being carried out at a temperature of 150°–280° C. and the temperature for the depolymerization being 30°–150° C. above that of the transesterification, and, optionally, recycling 50–100% of the amount of distillation residue obtained in the depolymerization into the transesterification reaction of (II) with (III), and optionally adding to the cyclic carbonate (I) after the depolymerization, one or more compounds selected from the group consisting of a) acids of sulfur and esters or salts thereof according to the formula

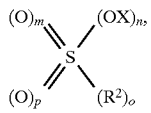 (III)

wherein
the indices m, n, o and p independently of one another denote the figure zero or one, but only two of these indices may simultaneously be zero,
X represents $Li^\oplus$, $Na^\oplus$, $K^\oplus$, $Rb^\oplus$, $Cs^\oplus$ or $N(R^3, R^4, R^5, R^6)^\oplus$, wherein $R^3$ to $R^6$ independently of one another denote H, $C_1$–$C_{18}$-alkyl, phenyl or benzyl, or represents $C_1$–$C_{18}$-alkyl, $C_6$–$C_{12}$-aryl or benzyl, where alkyl, aryl and benzyl can be substituted once or twice by methyl, ethyl, chlorine or $SO_3H$, and
$R^2$ assumes the meaning of —OX, —OOH, —$OSO_3$, —$OOSO_3$, —$NH_2$, —NH($SO_3H$), $C_1$–$C_{18}$-alkyl or $C_6$–$C_{12}$-aryl, which can be substituted in the manner mentioned, where, in the case where $R^2$ denotes OX not all the X denote one of the metal cations mentioned, and where $R^2$, in the case where n denotes zero, can also represent double-bonded oxygen, and b) acids of phosphorus and esters or salts thereof of the formula

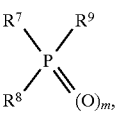 (IV)

wherein
m denotes the number zero or one,
$R^7$ represents $C_1$–$C_{20}$-(cyclo)alkyl, $C_6$–$C_{12}$-aryl or $C_7$–$C_{10}$-aralkyl, which can be substituted once or twice by O—$C_1$–$C_4$-alkyl, S—$C_1$–$C_4$-alkyl, COOH, CN, Cl, Br, $NH_2$, NH—$C_1$–$C_4$-alkyl, N($C_1$–$C_4$-alkyl)$_2$, NH—$C_6H_5$, N($C_1$–$C_4$-alkyl-P(O)(OH)$_2$)$_2$ or P(O)(OH)$_2$ or two different radicals of these, and in the (cyclo)alkyl contents of which one or two C atoms can be replaced by —O—, —S—, —NH—, —N($C_1$–$C_4$-alkyl)— or —CO— and/or two C atoms can be linked by a double or triple bond, and
$R^8$ and $R^9$ independently have the meaning OX,
$R^8$ furthermore can assume the scope of meaning of $R^7$ and $R^9$ can also denote H, and wherein $R^7$ and $R^8$ furthermore together can represent —O-arylene-O— or -arylene-O—, wherein arylene represents biphenylyl or —$C_6H_4$—$C_1$–$C_6$-(cyclo)alkylene-$C_6H_4$—,
X represents $H^\oplus$, $Li^\oplus$, $Na^\oplus$, $K^\oplus$, $Rb^\oplus$, $Cs^\oplus$ or $N(R^3, R^4, R^5, R^6)^\oplus$, wherein $R^3$ to $R^6$ independently of one another denote H, $C_1$–$C_{18}$-alkyl, phenyl or benzyl, or represents $C_1$–$C_{18}$-alkyl, $C_6$–$C_{12}$-aryl or benzyl, where alkyl, aryl and benzyl can be substituted once or twice by methyl, ethyl, chlorine or P(O)(OH)$_2$ and, provided that where two OX'$^s$ are present, not all of the X'$^s$ do not all denote one of the metal cations mentioned in an amount of 0.001–5% by weight, based on the amount of (I) for stablization against undesirable polymerization.

2. The process of claim 1, wherein instead of R and $R^1$, the radicals $R^{10}$ and $R^{11}$ occur, which are identical or different and denote H, $CH_3$, $C_2H_5$ or —$CH_2$—$OR^2$, wherein $R^2$ has the scope given in claim 1.

3. The process of claim 1, wherein instead of $R^3$, the radical $R^{13}$ occurs, which denotes phenyl, tolyl or chlorophenyl.

4. The process of claim 3, wherein $R^{13}$ denotes phenyl.

5. The process of claim 1, wherein 60 to 100% of the amount of the distillation residue are recycled into the transesterification.

6. The process of claim 5, wherein 70 to 100% of the amount of the distillation residue are recycled into the transesterification.

7. The process of claim 1, wherein the catalyst of the group consisting of tin, titanium and zirconium compounds is used in an amount of 0.03–0.1% by weight, based on the total amount of (II) and (III).

8. The process of claim 1, wherein the transesterification is carried out at a temperature of 150°–170° C.

9. The process of claim 1, wherein the depolymerization is carried out at a temperature of 190°–250° C.

10. The process of claim 9, wherein the depolymerization temperature is 200°–240° C.

11. The process of claim 1, wherein, in the case of stabilization of the cyclic carbonate, in addition to the S and P compounds of the type mentioned, one or more solvents from the group consisting of ethers, esters, ketones, nitriles, amides, lactams and lactones are added in an amount of 2–500% of the total weight of cyclic carbonate and S or P compound.

12. The process of claim 11, wherein one or more solvents from the group consisting of esters, amides, lactams and lactones are added.

13. The process of claim 11, wherein the solvent(s) is (are) added in an amount of 3–300% of the total weight of cyclic carbonate and S or P compound.

14. The process of claim 13, wherein the solvent(s) is (are) added in an amount of 5–200% of the total weight of cyclic carbonate and S or P compound.

15. The process of claim 1, wherein, in the case of stabilization, the acids of sulfur and esters and salts thereof employed are those of the formula $$\begin{array}{c} (O)_m \diagdown \diagup (OX)_n \\ S \\ \diagup \diagdown \\ (O)_p \quad (R^2)_o \end{array}$$

wherein the indices m, n, o and p independently of one another denote the figure zero or one, but only two of these indices may simultaneously be zero, X represents $H^\oplus$, $Li^\oplus$, $Na^\oplus$, $K^\oplus$, $Rb^\oplus$, $Cs^\oplus$ or $N(R^3, R^4, R^5, R^6)^\oplus$, wherein $R^3$ to $R^6$ independently of one another denote H, $C_1$–$C_{18}$-alkyl, phenyl or benzyl, or represents $C_1$–$C_{18}$-alkyl, $C_6$–$C_{12}$-aryl or benzyl, where alkyl, aryl and benzyl can be substituted once or twice by methyl, ethyl, chlorine or $SO_3H$, and $R^2$ assumes the meaning of —OX, —OOH, —OSO$_3$, —OOSO$_3$, —NH$_2$, —NH(SO$_3$H), $C_1$–$C_{18}$-alkyl or $C_6$–$C_{12}$-aryl, which can be substituted in the manner mentioned, where, in the case where $R^2$ denotes OX, not all the X denote one of the metal cations mentioned, and where $R^2$, in the case where n denotes zero, can also represent double-bonded oxygen, and the acids of phosphorus and esters or salts thereof employed are those of the formula $$\begin{array}{c} R^7 \diagdown \diagup R^9 \\ P \\ \diagup \diagdown \\ R^8 \quad (O)_m \end{array}$$

wherein m denotes the number zero or one, $R^7$ represents $C_1$–$C_{20}$-(cyclo)alkyl, $C_6$–$C_{12}$-aryl or $C_7$–$C_{10}$-aralkyl, which can be substituted once or twice by O—$C_1$–$C_4$-alkyl, S—$C_1$–$C_4$-alkyl, COOH, CN, Cl, Br, NH$_2$, NH—$C_1$–$C_4$-alkyl, N($C_1$–$C_4$-alkyl)$_2$, NH—$C_6$H$_5$, N($C_1$–$C_4$-alkyl-P(O)(OH)$_2$)$_2$ or P(O)(OH)$_2$ or two different radicals of these, and in the (cyclo)alkyl contents of which one or two C atoms can be replaced by —O—, —S—, —NH—, —N($C_1$–$C_4$-alkyl)— or —CO— and/or two C atoms can be linked by a double or triple bond, and $R^8$ and $R^9$ independently have the meaning OX, wherein X assumes the scope of meaning mentioned above in connection with formula (III), including the limitation with respect to the metal cations if two X are present, but wherein, in the context of the formula (IV), the substituent P(O)(OH)$_2$ occurs instead of the substituent SO$_3$H, and wherein $R^8$ furthermore can assume the scope of meaning of $R^7$ and $R^9$ can also denote H, and wherein $R^7$ and $R^8$ furthermore together can represent —O-arylene-O— or -arylene-O—, wherein arylene represents biphenylyl or —$C_6H_4$—$C_1$–$C_6$-(cyclo)alkylene-$C_6H_4$—.

16. The process of claim 1, wherein, in the case of stabilization, at least one compound from the group consisting of acids of phosphorus and esters and salts thereof is added to the cyclic carbonate.

17. The process of claim 1, wherein a stabilization of a cyclic carbonate of the formula $$\begin{array}{c} O-CH_2 \quad CH_2OH \\ \diagup \diagdown \diagup \\ O=C \quad C \\ \diagdown \diagup \diagdown \\ O-CH_2 \quad R^1 \end{array} \quad (VI)$$

in which

R denotes $C_1$–$C_6$-alkyl, cyclohexyl or $C_6$–$C_{12}$-aryl, is carried out.

18. A mixture of a cyclic carbonate of the formula (I) with at least one compound from the group consisting of acids of phosphorus and esters or salts thereof in amounts of 0.001 to 5% by weight of the sulfur and phosphorus compounds mentioned, based on the amount of cyclic carbonate, and optionally with an additional content of one or more solvents from the group consisting of ethers, esters, ketones, nitriles, amides, lactams or lactones in an amount of 2 to 500% of the total weight of cyclic carbonate and S or P compound.

19. The mixture of claim 18, wherein the solvent(s) is (are) from the group consisting of esters, amides, lactams and lactones.

20. The mixture of claim 18, wherein the solvent(s) is (are) present in an amount of 3 to 300% of the total weight of cyclic carbonate and S or P compound.

21. The mixture of claim 20, wherein the solvent(s) is (are) present in an amount of 5 to 200% of the total weight of cyclic carbonate and S or P compound.

22. A process for the preparation of an optionally stabilized cyclic carbonate of the formula (I)

$$\begin{array}{c} O-CH_2 \quad R \\ \diagup \diagdown \diagup \\ O=C \quad C \\ \diagdown \diagup \diagdown \\ O-CH_2 \quad R^1 \end{array} \quad (I)$$

in which

R and $R^1$ are identical or different and represent H, straight-chain or branched $C_1$–$C_6$-alkyl, $C_3$–$C_7$-cycloalkyl or —CH$_2$—OR$^2$, wherein $R^2$ represents H, $C_1$–$C_4$-alkyl, allyl, methallyl or benzyl and wherein two $R^2$ groups together can be —CH$_2$—, —CH(CH$_3$)—, —CH(C$_2$H$_5$)—, —CH(C$_6$H$_5$)— or —CH(C$_3$H$_7$)—, where $R^1$ can additionally denote $C_6$–$C_{12}$-aryl and where R and $R^1$ furthermore, together with the C atom on which they are substituents, can form a cyclopentane, cyclohexane, cycloheptane, oxetane, tetrahydrofuran, tetrahydro-pyran or dioxane ring, by transesterification of a 1,3-propanediol compound of the formula (II)

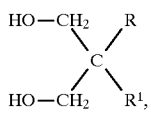

(II)

in which R and $R^1$ have the abovementioned meaning, with a carbonic acid ester of the formula (III)

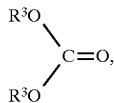

(III)

in which $R^3$ denotes $C_1$–$C_4$-alkyl or $C_6$–$C_{10}$-aryl, $R^3OH$ being split off, to give an oligo- or polycarbonate and, by subsequent distillative depolymerization of the oligo- or polycarbonate thus obtained, to give a cyclic carbonate (I), which comprises carrying out both the stage of transesterification and the subsequent distillative depolymerization in the presence of a tin compound as catalyst in an amount of 0.001–5% by weight, based on the total amount of (II) and (III), the transesterification being carried out at a temperature of 120°–180° C. and the depolymerization being carried out at a temperature of 150°–280° C. and the temperature for the depolymerization being 30°–150° C. above that of the transesterification, and recycling 50–100% of the amount of distillation residue obtained in the depolymerization into the transesterification reaction of (II) with (III), optionally adding to the cyclic carbonate (I) after the depolymerization, one or more compounds selected from the group consisting of a) acids of sulfur and esters or salts thereof according to the formula

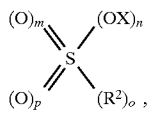

(III)

wherein the indices m, n, o and p independently of one another denote the figure zero or one, but only two of these indices may simultaneously be zero, X represents $Li^\oplus$, $Na^\oplus$, $K^\oplus$, $Rb^\oplus$, $Cs^\oplus$ or $N(R^3, R^4, R^5, R^6)^\oplus$, wherein $R^3$ to $R^6$ independently of one another denote H, $C_1$–$C_{18}$-alkyl, phenyl or benzyl, or represents $C_1$–$C_{18}$-alkyl, $C_6$–$C_{12}$-aryl or benzyl, where alkyl, aryl and benzyl can be substituted once or twice by methyl, ethyl, chlorine or $SO_3H$, and $R^2$ assumes the meaning of —OX, —OOH, —$OSO_3$, —$OOSO_3$, —$NH_2$, —$NH(SO_3H)$, $C_1$–$C_{18}$-alkyl or $C_6$–$C_{12}$-aryl, which can be substituted in the manner mentioned, where, in the case where $R^2$ denotes OX, not all the X denote one of the metal cations mentioned, and where $R^2$, in the case where n denotes zero, can also represent double-bonded oxygen, and b) acids of phosphorus and esters or salts thereof of the formula

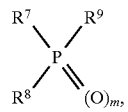

(IV)

wherein m denotes the number zero or one, $R^7$ represents $C_1$–$C_{20}$-(cyclo)alkyl, $C_6$–$C_{12}$-aryl or $C_7$–$C_{10}$-aralkyl, which can be substituted once or twice by O—$C_1$–$C_4$-alkyl, S—$C_1$–$C_4$-alkyl, COOH, CN, Cl, Br, $NH_2$, NH—$C_1$–$C_4$-alkyl, $N(C_1$–$C_4$-alkyl$)_2$, NH—$C_6H_5$, $N(C_1$–$C_4$-alkyl-P(O)(OH)$_2)_2$ or P(O)(OH)$_2$ or two different radicals of these, and in the (cyclo)alkyl contents of which one or two C atoms can be replaced by —O—, —S—, —NH—, —N($C_1$–$C_4$-alkyl)— or —CO— and/or two C atoms can be linked by a double or triple bond, and $R^8$ and $R^9$ independently have the meaning OX, $R^8$ furthermore can assume the scope of meaning of $R^7$ and $R^9$ can also denote H, and wherein $R^7$ and $R^8$ furthermore together can represent —O0arylene-O— or -arylene-O—, wherein arylene represents biphenylyl or —$C_6H_4$—$C_1$–$C_6$-(cyclo) alkylene-$C_6H_4$—, X represents $H^\oplus$, $Li^\oplus$, $Na^\oplus$, $K^\oplus$, $Rb^\oplus$, $Cs^\oplus$ or $N(R^3, R^4, R^5, R^6)^\oplus$, wherein $R^3$ to $R^6$ independently of one another denote H, $C_1$–$C_{18}$-alkyl, phenyl or benzyl, or represents $C_1$–$C_{18}$-alkyl, $C_6$–$C_{12}$-aryl or benzyl, where alkyl, aryl and benzyl can be substituted once or twice by methyl, ethyl, chlorine or P(O)(OH)$_2$ and, provided that where two OX'$^s$ are present, not all of the X'$^s$ do not all denote one of the metal cations mentioned in an amount of 0.001–5% by weight, based on the amount of (I) for stablization against undesirable polymerization.

* * * * *

UNITED STATES PATENT AND TRADEMARK OFFICE
CERTIFICATE OF CORRECTION

PATENT NO. : 5,861,107
DATED : January 19, 1999
INVENTOR(S) : Hans-Josef Buysch, et al.

It is certified that error appears in the above-identified patent and that said Letters Patent is hereby corrected as shown below:

Col. 22, Line 33     Delete "-O0arylene-O-" and substittue -- -O-arylene-O --

Signed and Sealed this

Sixteenth Day of November, 1999

Attest:

Attesting Officer

Q. TODD DICKINSON

Acting Commissioner of Patents and Trademarks